United States Patent
Biedermann et al.

(10) Patent No.: US 10,092,335 B2
(45) Date of Patent: Oct. 9, 2018

(54) METHOD OF USING TEMPLATE IN MANUFACTURING AN IMPLANT FOR SPINAL OR OTHER ORTHOPEDIC FIXATION

(71) Applicant: BIEDERMANN TECHNOLOGIES GMBH & CO. KG, Donaueschingen (DE)

(72) Inventors: Lutz Biedermann, VS-Villingen (DE); Achim Zipse, Baden-Baden (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 149 days.

(21) Appl. No.: 15/134,196

(22) Filed: Apr. 20, 2016

(65) Prior Publication Data

US 2016/0310178 A1    Oct. 27, 2016

Related U.S. Application Data

(60) Provisional application No. 62/150,636, filed on Apr. 21, 2015.

(30) Foreign Application Priority Data

Apr. 21, 2015    (EP) .................................... 15164551

(51) Int. Cl.
*A61B 17/80*    (2006.01)
*B23P 25/00*    (2006.01)
(Continued)

(52) U.S. Cl.
CPC .......... *A61B 17/80* (2013.01); *A61B 17/7001* (2013.01); *A61B 17/7002* (2013.01); *A61B 17/7059* (2013.01); *B23P 25/00* (2013.01); *A61B 2017/00867* (2013.01); *A61F 2210/0014* (2013.01); *Y10T 29/49865* (2015.01)

(58) Field of Classification Search
CPC . A61B 17/7059; A61B 17/7002; A61B 17/80; A61B 17/7011; A61F 2210/0014; B23P 25/00; Y10T 29/49865
See application file for complete search history.

(56) References Cited

U.S. PATENT DOCUMENTS

| | | |
|---|---|---|
| 4,170,990 A | 10/1979 | Baumgart et al. |
| 5,290,289 A | 3/1994 | Sanders et al. |

(Continued)

OTHER PUBLICATIONS

Extended European Search Report issued by the EPO for EP 15164551.2 dated Oct. 13, 2015; (7 pages).

*Primary Examiner* — Jermie Cozart
(74) *Attorney, Agent, or Firm* — Lewis Roca Rothgerber Christie LLP

(57) ABSTRACT

A template for use in producing an implant for use in spinal or other orthopedic fixation is provided, where the template is adjustable between a first configuration in which the template is capable of bending in response to a force and is capable of retaining a bent shape, and a second configuration in which the template assumes a memorized shape in response to directing the temperature of the template to value that is at or above a recovery level, where the recovery level is above body temperature. A spinal or orthopedic implant is formed by duplicating the bent shape of the template.

13 Claims, 3 Drawing Sheets

(51) Int. Cl.
*A61B 17/70* (2006.01)
*A61B 17/00* (2006.01)

(56) References Cited

U.S. PATENT DOCUMENTS

| | | | | |
|---|---|---|---|---|
| 5,647,872 | A * | 7/1997 | Gilbert | A61B 17/7059 |
| | | | | 606/280 |
| 6,221,077 | B1 | 4/2001 | Rinner et al. | |
| 2007/0161997 | A1* | 7/2007 | Thramann | A61B 17/7007 |
| | | | | 606/86 A |
| 2007/0191831 | A1 | 8/2007 | Sanders et al. | |
| 2010/0063548 | A1 | 3/2010 | Wang | |
| 2012/0065687 | A1* | 3/2012 | Ballard | A61B 17/7004 |
| | | | | 606/259 |
| 2013/0231703 | A1* | 9/2013 | Seme | A61B 17/70 |
| | | | | 606/252 |

* cited by examiner

METHOD OF USING TEMPLATE IN MANUFACTURING AN IMPLANT FOR SPINAL OR OTHER ORTHOPEDIC FIXATION

CROSS-REFERENCE TO RELATED APPLICATIONS

The present application claims the benefit of U.S. Provisional Application Ser. No. 62/150,636, filed Apr. 21, 2015, the contents of which are hereby incorporated by reference in their entirety, and claims priority from European Patent Application EP 15 164 551.2, filed Apr. 21, 2015, the contents of which are hereby incorporated by reference in their entirety.

BACKGROUND

Field

The present disclosure relates to a template for use in manufacturing an implant for spinal or other orthopaedic fixation and to a method of manufacturing such an implant. The template is capable of bending in response to a force and is capable of retaining a bent shape, which is used as a model for an implant. The implant is bent to have a shape corresponding to the shape of the template.

Description of Related Art

Spinal rod templates are used for modelling the shape of a permanent rod that is used for stabilizing the spine by means of a screw-rod system. The necessary shape and length of the permanent spinal rod to be implanted into a patient is determined on the basis of a rod template, which is a rod that is initially bent and measured to conform to a desired part of the patient's spine. The rod template is then utilized to shape the permanent rod to be implanted into the patient and secured to a portion of the length of the spine. Such templates are, for example, known from U.S. Pat. No. 6,221,077 B1.

The rod templates are bent manually or with a tool in an operating room. To permit bending in the operating room, rod templates known in the art can be made of an aluminium alloy, for example AlMgSi, having a relatively low strength. After use in the manufacture of the permanent rod implants, the rod templates are bent back (e.g., to an original shape) and sterilized for a second use. This procedure may be repeated several times. However, the used rod templates may still have a remaining curvature different from the rod's original shape. In addition, there may be a risk of breaking the rod templates when they are bent and bent back several times.

US 2010/0063548 A1 describes a spinal correction template having a first configuration which substantially corresponds to an uncorrected shape of a spine. The spinal correction template can be attached to a patient's spine and activated such that the template achieves a second configuration to cause the spine to assume an orientation substantially corresponding to the second configuration. In one embodiment, the spinal correction template can be formed of a shape-memory alloy such as Nitinol. The step of activating occurs at a temperature in the range of about 28° C. to about 37° C. Hence, the template can have an austenite finish temperature $A_f$ that is below body temperature (about 37° C.). A spinal correction method using the template further includes attaching a primary spinal rod to at least a portion of the patient's spine after the spine achieves a corrected orientation with the template, and removing the spinal correction template. A secondary spinal rod may be inserted in place of the spinal correction template. In some embodiments, the spinal correction template can remain in the patient's body.

SUMMARY

Embodiments of the invention provide a template for use in manufacturing an implant for spinal or other orthopaedic fixation that is bendable in an operating room at about room temperature and that is reusable several times. Further, a method of manufacturing such a template and a method of manufacturing an implant with such a template is provided.

The template is configured to change its configuration between a first configuration and a second configuration. In the first configuration, the template is capable of bending in response to a force and is capable of retaining a bent shape. In the second configuration, the template assumes a memorized shape in response to directing the temperature of the template to a value at or above a recovery level, where the recovery level is above body temperature. Body temperature means a temperature of around 37° C. Hence, the template is in the first configuration during its intended use of bending in the operating room, and may be bent outside or inside a patient's body.

In the first configuration, the template may be bent or contoured in the operating room with low force to reproduce a curvature of a section of a patient's spine that has to be corrected or the shape of a bone plate which is intended to bridge bone parts or bones to be immobilized. The template may be bent or contoured in the operating room either manually or using a tool. The template can be bent or contoured before or while surgery takes place. After the template is bent or contoured into a desired shape, the implant can be manufactured by duplicating the shape of the template using a material for the implant that is different than the material of the template and applying higher forces to the implant than the template (e.g., with a tool).

Using the template, difficult shapes can be easily reproduced in the implant and an improved anatomical contour can be obtained.

In the second configuration, the memorized shape of the template, such as a straight or even shape, can be easily achieved by heating the template to a temperature at or above the recovery level such that the template automatically assumes the memorized shape. A step of bending the template back to an original shape is unnecessary. After recovery of the memorized shape, the template may be re-used for another procedure. The transformation from the first configuration to the second configuration and vice-versa is reversible. As such, the template can be re-used a great, even an unlimited number of times. Moreover, an active cooling step is not needed to achieve the first configuration. If the temperature of the template is not kept at or above the recovery level, the temperature of the template automatically decreases (e.g., to room temperature) and the template assumes the first configuration where the template is deformable (i.e., easily bent or contoured).

Further, it is possible to revise the formed shape of the template through mild heating to a temperature below the recovery level.

The template may be, for example, a spinal rod or a bone plate. A rod template may be used for producing a spinal rod for correcting a deformity or misalignment in the spinal column caused by disorder such as, for example, scoliosis or caused by injuries. Templates for producing bone plates with a bent shape may be used, for example, for correcting fractures of the hand or the shoulder.

In one or more embodiments, the template is made of a nickel-titanium (NiTi) alloy with an austenite finish temperature $A_f$ above body temperature, in particular above 45° C., preferably above 50° C., more preferably above 60 C and more preferably about 70° C. to about 80° C. Hence, the template may be placed in the second configuration with the memorized shape by sterilizing the template with a typical procedure for sterilizing medical instruments, such as vapour sterilization or by immersing the template in hot water. Thereby, heating the template to a temperature at or above the recovery level to attain the memorized shape is easily achieved. The NiTi alloy is biocompatible, and therefore, the template is usable inside and outside the human body.

In one or more embodiments, the NiTi alloy includes around 49.0 to 52.0 at. % (atomic percent) nickel, and in one or more embodiments, the NiTi alloy includes around 49.5-50.0 at. % nickel. The remainder of the NiTi alloy is titanium. Hence, the NiTi alloy is a martensitic shape memory alloy that has a martensite finish temperature $M_f$ above room temperature. Room temperature means a temperature of around 23° C.±3° C.

The strength, in particular the bending stiffness of the template in the first configuration, is less than that of conventional aluminum-magnesium-silicon (AlMgSi) alloy templates. Hence, the template in the first configuration can be bent with less force than is required to bend conventional AlMgSi alloy templates.

The template can be manufactured in a simple manner including conventional steps of hot drawing and annealing. Thereafter, the template may be cut to size, laser marked, and cleaned.

During manufacturing, a surface of the template may obtain an oxide layer, in particular during an annealing step. The oxide layer has a colour that differs from the colour of the surfaces of the implants. Therefore, the template can be easily visually distinguished from the implants. The oxide layer also allows laser marking and imprinting other markings, such as length scales.

In the case of the NiTi template, the detection under X-rays is improved due to a higher density compared to the conventional AlMgSi templates.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
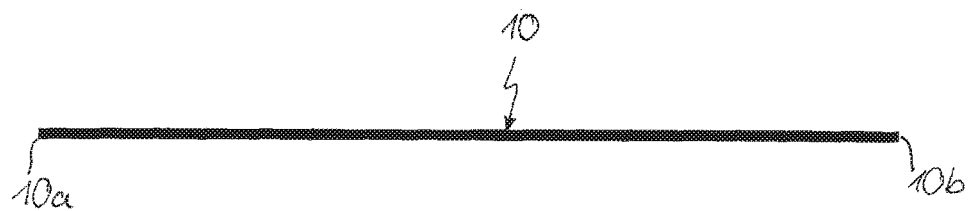
FIG. 1 shows a schematic view of a first embodiment of the template in a second configuration.
Figure 2:
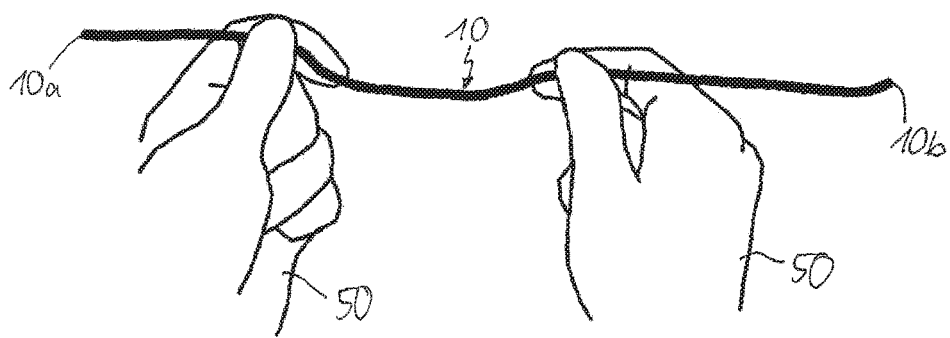
FIG. 2 shows a schematic view of the first embodiment of the template in a first configuration.

Referring to FIGS. 1 and 2, a first embodiment of the template includes a rod 10. The rod 10 extends between opposite ends 10a, 10b. The rod 10 may have a cylindrical shape throughout its length and may have a constant cross-sectional diameter through its entire length. However, it shall be understood that the rod 10 may have any cross-sectional shape deviating from a cylindrical shape and may have a constant cross-sectional shape, or may have a cross-sectional shape that varies along a length of the rod 10. The rod 10 may be solid, for example, without cavities inside or at the surface of the rod 10.

As described more fully below, the rod 10 includes a shape memory material that is characterized by having two distinct configurations and the ability to restore itself to a memorized shape that has been pre-configured, for example by heating the rod to a temperature at or above a recovery level.

In a second configuration, shown in FIG. 1, the rod 10 assumes a memorized shape. In the embodiment shown in FIG. 1, the memorized shape is a straight shape. However, any other pre-configured memorized shape can be contemplated, such as a shape with a slight curvature between the ends 10a, 10b. The rod 10 is configured to assume the second configuration in response to directing the temperature of the rod 10 to a value at or above a recovery level. The rod 10 is configured to maintain the memorized shape when the temperature of the rod 10 is at or above the recovery level.

FIG. 2 shows the rod 10 in a first configuration in which the rod 10 is capable of bending in response to a force, such as a force exerted by the hands 50 of a user. In the first configuration, the rod 10 is capable of retaining a bent shape when the bending force is no longer applied to the rod 10. The rod 10 is in the first configuration at a temperature that is less than the recovery level, for example at body temperature or less, such as at room temperature.

The material of the rod 10 is a shape memory alloy. In some embodiments, the rod 10 may be a nickel-titanium alloy (NiTi alloy) exhibiting the shape memory effect. In the first configuration, the material of the template is in a martensitic metallurgical state where the rod 10 is flexible and deformable and can assume a variety of shapes. Hence, in the first configuration, the rod 10 can be bent by exerting a low force onto the rod 10, for example manually, to cause the rod 10 to assume a bent shape. By directing the temperature of the rod 10 to a value at or above the recovery level (i.e., by heating the rod 10 to a temperature at or above the recovery level), the material of the template assumes the austenitic metallurgical state where the rod 10 is rigid and assumes the memorized shape. The temperature at which the material begins to transform into the austenitic metallurgical state is the austenite start temperature $A_s$ and the temperature at which the material has fully transformed into the austenitic metallurgical state is the austenite finish temperature $A_f$. In embodiments where the rod 10 is an NiTi alloy, the recovery level can be defined as the austenite finish temperature $A_f$.

When the temperature of the rod 10 falls below the temperature of the recovery level, the material of the template reaches the martensite start transformation temperature $M_s$ where the austenitic metallurgical structure begins to transform into the martensitic metallurgical structure. At the martensite finish temperature $M_f$, the alloy is completely converted into the martensitic state. When the rod is reheated, a transformation back to the austenitic structure begins at the austenite start temperature $A_s$ and is completed at the austenite finish temperature $A_f$. In embodiments where the rod 10 is an NiTi alloy, the transition temperatures $A_f$, $A_s$, $M_f$ and $M_s$ may be determined with a method according to ASTM F2082-06, titled "Standard Test Method for Determination of Transformation Temperature of Nickel-Titanium Shape Memory Alloys by Bend and Free Recovery."

In one or more embodiments, the austenite finish temperature $A_f$ is selected to be above body temperature, for example above 45° C., preferably above 50° C., more preferably above 60° C. and most preferably between about 70° C. to about 80° C. An upper limit of the austenite finish temperature $A_f$ may be about 90° C. to about 100° C. The martensite finish temperature $M_f$ is preferably above room temperature. The martensite finish temperature $M_f$ is dependent on the austenite finish temperature $A_f$ of the material of the template. For example, a template having an austenite finish temperature $A_f$ of about 80° C. may have an austenite start temperature $A_s$ temperature of about 60° C., a martensite start temperature $M_s$ of about 50° C. and a martensite finish temperature $M_f$ of about 40° C.

A particular example for the shape memory alloy material of the rod 10 according to the first embodiment is a martensitic nickel titanium alloy with a nickel content that is less than that of nickel titanium alloys having superelastic properties, i.e., less than about 50.6 to 51.0 at. % nickel according to the standard ASTM F 2063. For example, the nickel content of the alloy material of the template according to one or more embodiments is 49.0 to about 52.0 at %-nickel. In some embodiments, the nickel content of the alloy material of the template is about 49.5 to about 50.0 at. % nickel. The remainder of the alloy is titanium. Small portions of impurities may be present as listed in ASTM F 2063. An example of such an alloy is SM 495, which may be deformed at room temperature and is transformed back to the austenitic metallurgical state at an austenite finish temperature $A_f$ higher than body temperature.

The rod 10 may have an oxide layer on its surface that is obtained through annealing during a step of manufacturing the rod 10. The oxide layer may have a color that is darker than conventional oxide layers of permanent implants. This results from the fact that the oxide layer obtained through annealing is thicker than conventional oxide layers on implants that may be obtained by anodic oxidation. The oxide layer may represent a marking to distinguish the rod 10 from implants by the color of the rod 10.

On the surface of the rod 10, markings (not shown) may be provided that are obtainable by laser marking. Such markings may include CE marking, LOT-number marking and/or other markings. For example, the rod 10 may have incremental distance markings.

A flexural strength of the rod 10 in the first configuration may be, for example, around 100-150 N/mm². The rod 10 may have a diameter corresponding to diameters of spinal correction rods, for example, a diameter of 3.5 mm, 4.5 mm, 5.5 mm, and the like. The density of the material of the rod 10 may be considerably higher than that of conventional AlMgSi rods, for example, around 6 g/cm³ or higher. The higher density results in improved detection through X-rays.

A method of manufacturing the template rod 10 includes steps of forming a pre-configured shape and memorizing the pre-configured shape such that the template has the pre-configured memorized shape in the austenitic metallurgical state. The manufacturing steps include hot drawing and annealing. Typical conditions for annealing are annealing at around 350° C. to around 800° C. for around 5 minutes to around 60 minutes. Suitable conditions may be selected depending on the specific composition of the alloy of the rod 10. The oxide layer is obtained during the annealing step. The method may further include steps of cutting to size and/or of laser marking and/or of cleaning the template.

Figure 3:
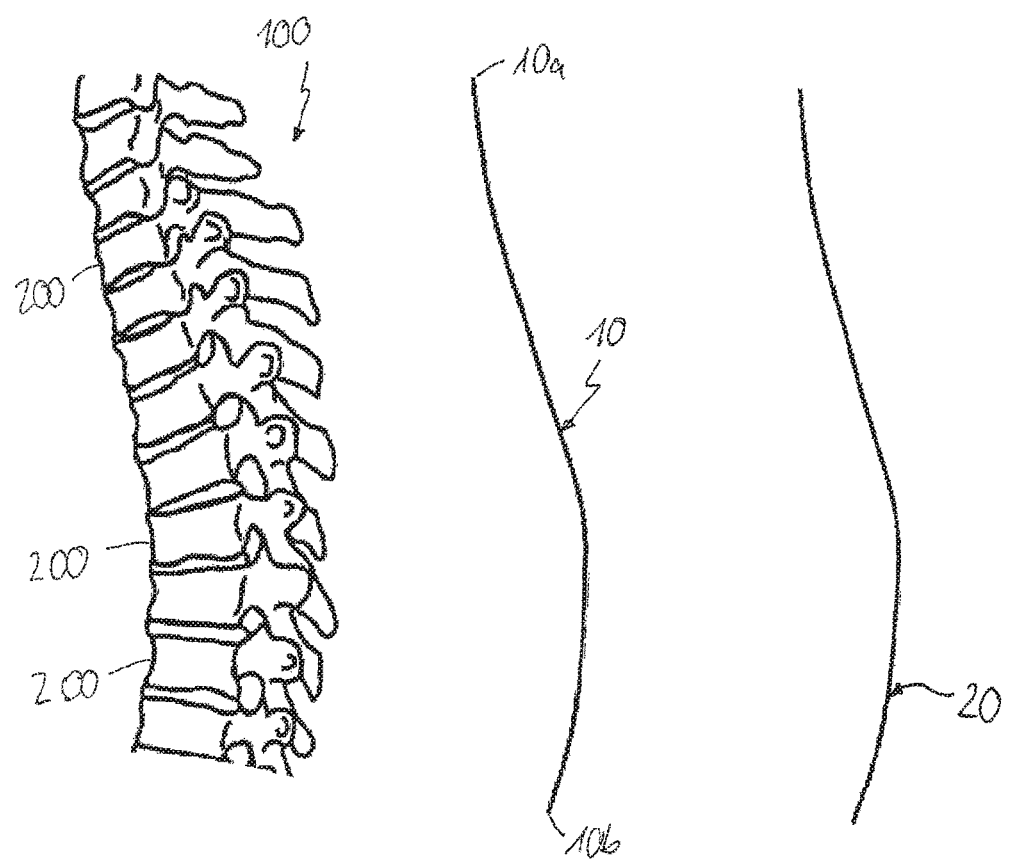
FIG. 3 shows a schematic view of the template of the first embodiment adapted to a desired curvature of a portion of a spinal column to be treated, and an implant produced using the template.

Turning now to FIG. 3, use of the template is shown schematically. The rod 10 is bent in the operating room along the actual curvature or the desired curvature of a portion of the spinal column 100, including a number of vertebrae 200. Because the operating room is normally at room temperature, the rod 10 is in the martensitic metallurgical state in the operating room where the rod 10 can be easily bent manually or with a device. Alternatively, the rod 10 can be inserted into bone anchors (not shown) implanted in the vertebrae to be stabilized. In this case, the rod 10 can be bent in the body of the patient. Because the temperature of the recovery level is above body temperature (about 37° C.), the rod 10 is still in the martensitic metallurgical state when in the body of the patient. After the desired curvature is achieved, the rod 10 forms the template for a permanent spinal rod 20 that is bent to have a duplicate shape of the rod 10. Bending of the rod 20 may be performed with a device. The permanent spinal rod 20 is then inserted into the bone anchors (not shown) to stabilize the portion of the spine to be treated.

Figure 4:
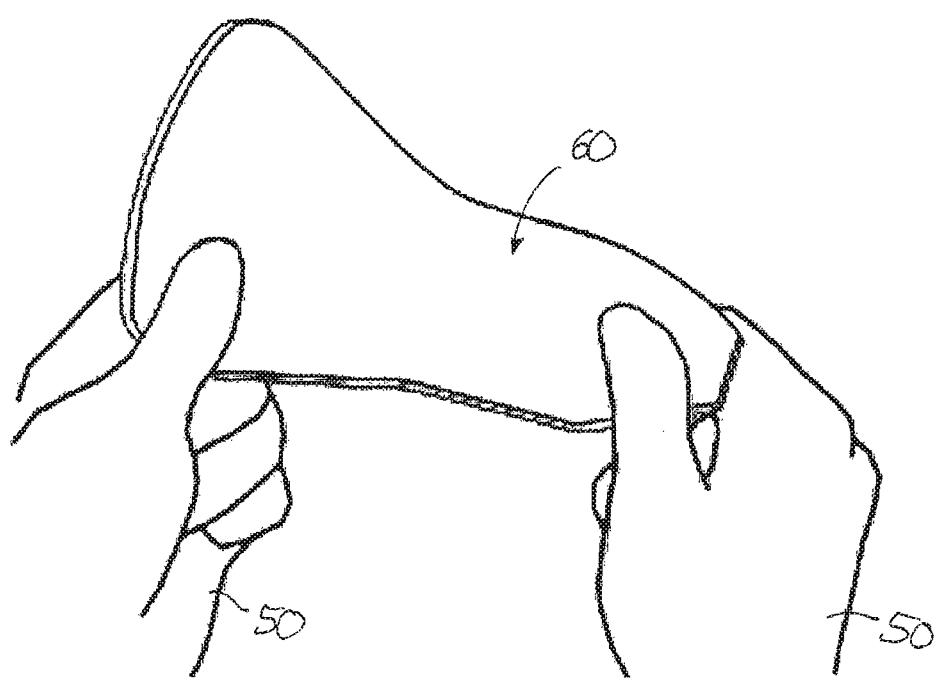
FIG. 4 shows a schematic perspective view of a second embodiment of the template in a first configuration.

Turning now to FIG. 4, a second embodiment of the template is shown, which is in the form of a bone plate 60. The bone plate 60 as shown has an elongate shape, i.e. the greatest length of the bone plate 60 is larger than the greatest width of the bone plate 60. The thickness of the bone plate 60 is such that the bone plate 60 can be bent in the first configuration, as depicted in FIG. 4, by exerting a force with the user's hands 50. It should be appreciated that the thickness of the bone plate 60 does not need to be identical to the thickness of a permanent bone plate implant to be manufactured using the template bone plate 60. The bone plate 60 is made of the same material as the rod 10 according to the first embodiment. Hence, the properties of the bone plate 60 with regard to the first configuration and the second configuration are identical. In the second configuration, the bone plate 60 is in the memorized shape, which may be a straight shape, but can also be a slightly bent shape. The contour of the bone plate 60 can be any contour, such as rectangular, irregular, square, oval, and the like.

The method of manufacturing the bone plate 60 and the method of producing a permanent bone plate implant using the bone plate 60 are the same as described for the first embodiment.

Further modifications of the above described embodiments may be contemplated. For example, instead of spinal rods or bone plates, any other orthopaedic components or implants may be manufactured using a correspondingly shaped template, such as bone nails or pegs or hooks.

Instead of a nickel titanium alloy, other shape memory alloys or shape memory polymers (SMPs) can be used. Such shape memory polymers may include linear block copolymers, for example shape memory polyurethane, thermoplastic polymers, for example polynorbornene, or chemically cross-linked SMPs. The recovery level is then defined as the temperature at which the material begins to transform into the second configuration to reach the memorized shape.

The memorized shape can be any shape. Hence, bending the template and the resulting bent shape of the template in the first configuration includes deviating from the memorized shape.

The invention claimed is:

1. A method of using a template to form an implant for spinal or other orthopaedic fixation, wherein the implant is separate from the template, the template being adjustable between a first configuration wherein the template is bendable in response to a force and is capable of retaining a bent shape, and a second configuration wherein the template assumes a memorized shape in response to directing a temperature of the template to be at or above a recovery level, wherein the temperature of the recovery level is above body temperature, the method comprising:

bending the template to a shape for spinal or other orthopaedic fixation when the template is in the first configuration;

bending the separate implant to the shape of the template in the first configuration while holding the template in the first configuration; and heating the template to a temperature at or above the recovery level after bending the separate implant to the shape of the template and when the template is outside of a human body, to cause the template to assume the memorized shape of the second configuration.

2. The method of claim 1, wherein the step of bending the template to a shape when the template is in the first configuration comprises bending the template to an actual curvature of a portion of a spinal column.

3. The method of claim 1, wherein the step of bending the template to a shape when the template is in the first configuration comprises bending the template to a desired curvature of a portion of a spinal column.

4. The method of claim 1, wherein the shape of the template is a rod or a plate, wherein the memorized shape is a substantially straight shape, and wherein the step of heating the template to a temperature at or above the recovery level comprises heating the template to cause the template to assume the substantially straight shape.

5. The method of claim 1, wherein the template comprises a shape memory material, wherein the step of heating the template to a temperature at or above the recovery level comprises heating the template to an austenite finish temperature $A_f$ of the template, and wherein the austenite finish temperature $A_f$ is above 45° C.

6. The method of claim 1, wherein the template is made of a nickel-titanium shape memory alloy, wherein the template is in a martensitic state in the first configuration, wherein the template is in the first configuration at room temperature, and wherein the method comprises cooling the template to room temperature to cause the template to assume the first configuration before bending the template to a desired shape for spinal or other orthopaedic surgery.

7. The method of claim 1, wherein the temperature of the recovery level is above 45° C.

8. The method of claim 1, wherein the temperature of the recovery level is above 60° C.

9. The method of claim 1, wherein the temperature of the recovery level is between 70° C. and 80° C.

10. The method of claim 1, wherein the step of heating the template to a temperature at or above the recovery level comprises heating the template while in the first configuration to a temperature above the temperature of the recovery level.

11. The method of claim 10, wherein the step of heating the template to a temperature above the recovery level comprises heating the template during a sterilization process.

12. The method of claim 11, wherein the sterilization process comprises vapour sterilization or immersing the template in a hot fluid.

13. The method of claim 1, further comprising cooling the template to room temperature such that the template assumes the first configuration.

* * * * *